United States Patent
Higo

(10) Patent No.: US 6,690,172 B2
(45) Date of Patent: Feb. 10, 2004

(54) MULTIPLE ELECTRIC CONDUCTIVITY MEASURING APPARATUS

(75) Inventor: Yuji Higo, Tokyo (JP)

(73) Assignee: Organo Corporation, Tokyo (JP)

( * ) Notice: Subject to any disclaimer, the term of this patent is extended or adjusted under 35 U.S.C. 154(b) by 59 days.

(21) Appl. No.: 10/009,395

(22) PCT Filed: Feb. 15, 2001

(86) PCT No.: PCT/JP01/01073

§ 371 (c)(1),
(2), (4) Date: Oct. 22, 2001

(87) PCT Pub. No.: WO01/63268

PCT Pub. Date: Aug. 30, 2001

(65) Prior Publication Data

US 2003/0098690 A1 May 29, 2003

(30) Foreign Application Priority Data

Feb. 23, 2000 (JP) .......................................... 2000-45374

(51) Int. Cl.[7] .............................................. G01R 27/22
(52) U.S. Cl. ........................ 324/439; 324/450; 324/691
(58) Field of Search ................................. 324/439, 442, 324/444, 450, 687, 654, 688, 691; 73/862.628, 61.21

(56) References Cited

U.S. PATENT DOCUMENTS

| | | | | |
|---|---|---|---|---|
| 3,993,945 A | * | 11/1976 | Warmoth et al. | 324/449 |
| 4,262,253 A | * | 4/1981 | Clark | 324/439 |
| 4,757,252 A | * | 7/1988 | Maltby et al. | 324/687 |
| 5,008,627 A | * | 4/1991 | Tsutsuta et al. | 324/444 |
| 5,223,796 A | * | 6/1993 | Waldman et al. | 324/687 |
| 6,264,825 B1 | * | 7/2001 | Blackburn et al. | 205/777.5 |

* cited by examiner

Primary Examiner—N. Le
Assistant Examiner—Vincent Q. Nguyen
(74) Attorney, Agent, or Firm—Norris McLaughlin & Marcus

(57) ABSTRACT

A multiple electric conductivity measuring apparatus having at least two electric conductivity measuring cells each having at least two electrodes brought into contact with a substance to be measured, wherein the electric conductivity measuring cells are so connected electrically that the sensing signals therefrom can be added and/or subtracted. The measuring apparatus can measure a micro difference or variation of the electric conductivity between a plurality of measuring points different in position or time with high reliability, accuracy and sensitivity.

3 Claims, 8 Drawing Sheets

MULTIPLE ELECTRIC CONDUCTIVITY MEASURING APPARATUS

This application is a 371 of PCT/JP01/01073 filed on Feb. 15, 2001.

TECHNICAL FIELD OF THE INVENTION

The present invention relates to a multiple electric conductivity measuring apparatus having a plurality of electric conductivity measuring cells, and more specifically, relates to a multiple electric conductivity measuring apparatus capable of accurately measuring a difference or variation of the electric conductivities between measuring points different in position or time in a treatment system containing a substance to be measured such as an aqueous solution and the like.

BACKGROUND ART OF THE INVENTION

Electric conductivity is especially employed as a scale to measure a concentration of ions capable of migrating in an aqueous solution, and an electric conductivity measuring apparatus is used to measure ion concentrations in many kinds of aqueous solutions. An electric conductivity measuring apparatus, generally, determines an increase or a decrease of the ion concentration of an aqueous solution to be measured by measuring the resistance of the aqueous solution existing between an electric conductivity detection electrode and an electric current supply electrode connected to a power source.

As a method for using a conventional electric conductivity measuring apparatus, the electric conductivity measuring apparatus is installed at a predetermined measuring point, or a sample solution is introduced from a predetermined measuring point into the electric conductivity measuring apparatus, and the electric conductivity measured by the apparatus is utilized for observing the condition of an aqueous solution or controlling the water quality thereof and the like in many kinds of fields. In the measurement of electric conductivity by the electric conductivity measuring apparatus, usually, the measurement is conducted after adjusting the measuring range of the electric conductivity measuring apparatus in accordance with a condition of a substance to be measured, a condition of an electrode, a condition of the circumstances at the time of the measurement (for example, an ambient temperature or a condition of noises from surrounding equipment) and the like. Further, in this measurement, a surface condition of the electrode often varies with time since organic substances and the like contained in a substance to be measured onto the electrode of the electric conductivity measuring apparatus. In such a condition, a drift from a desired measuring standard point occurs more or less during the measurement. Therefore, the data of the electric conductivity measured by the electric conductivity measuring apparatus are deemed to be data which are relatively low in reliability as data used for operation management or control, and it is the present situation that the data are considered as secondary data.

Especially, in a case where measurement data of electric conductivity are collected from a plurality of measuring points, and, for example, a progress degree of a treatment of an aqueous solution between the plural measuring points, or a variation of water quality between these measurement points, and further, in a case where a variation of the electric conductivity with time is measured at a substantially identical measuring position, practically it is difficult to measure with a high accuracy, because the measuring range of each apparatus is adjusted, or a drift occurs with time, as described above. Further, when a variation of electric conductivity, or a difference in electric conductivities between a plurality of measuring points is to be measured, in a case where the variation or the difference is much smaller than the absolute value of the electric conductivity which is being measured, since the measuring range is adjusted relative to the relatively great absolute value of the electric conductivity, it is very difficult to distinguish such a micro variation or difference, or, the measured data become low in reliability. In practice, however, there are many requirements to measure such a micro difference or variation between two or a plurality of measuring points different in position or time. If such a micro difference or variation can be measured with a high reliability, a high accuracy and a high sensitivity, it is considered that the use is very broad. However, an electric conductivity measuring apparatus capable of satisfying such requirements has not yet been found.

DISCLOSURE OF THE INVENTION

Accordingly, it is an object of the present invention to provide a multiple electric conductivity measuring apparatus capable of measuring a micro difference or variation of electric conductivity between a plurality of measuring points different in position or time with a high reliability, a high accuracy and a high sensitivity to satisfy the above-described requirements.

To accomplish the above-described object, a multiple electric conductivity measuring apparatus according to the present invention comprises at least two electric conductivity measuring cells each having at least two electrodes brought into contact with a substance to be measured, the electric conductivity measuring cells are so connected electrically that sensing signals themselves from the electric conductivity measuring cells can be treated to be added and/or subtracted.

Namely, in a conventional electric conductivity measuring apparatus, a sensing signal from one electric conductivity measuring cell is amplified by an amplifier and the like, and the amplified signal is rectified into a signal with an appropriate level as an output signal for measuring an electric conductivity, and when a plurality of electric conductivity measuring apparatuses are installed, it has been necessary to adjust a measuring range for each electric conductivity measuring apparatus. In the multiple electric conductivity measuring apparatus according to the present invention, however, within the apparatus itself, an electrical calculation treatment such as addition, subtraction and the like is performed with respect to the sensing signals themselves sent from the respective electric conductivity measuring cells, and the signal after the treatment is amplified as needed, and is output as a difference or variation between the electric conductivities measured at the respective electric conductivity measuring cells. Therefore, the multiple electric conductivity measuring apparatus according to the present invention is basically and distinctly different from the conventional technology in that the conventional electric conductivity measuring apparatuses are merely disposed in plural form and a difference or variation between the data measured by the apparatuses is obtained.

In this multiple electric conductivity measuring apparatus according to the present invention, the above-described at least two electrodes in each electric conductivity measuring cell can be constructed from an electric conductivity detection electrode and an electric current supply electrode. The two-electrode formation itself as the constitution of the electrode is heretofore known. To the electric current supply electrode, for example, an AC current is supplied. In a case where a plurality of electric current supply electrodes are disposed, an amplified or attenuated AC current may be supplied to at least one electric current supply electrode. If an AC current is amplified before being supplied to an electric current supply electrode, it can create substantially the same condition that the supplied electric current is multiplied by a predetermined magnification, and the same effect of the multiplication can be obtained also on sensing signals sent from the electric conductivity measuring cells. If an AC current is attenuated before being supplied to an electric current supply electrode, it can create substantially the same condition that the supplied electric current is divided by a predetermined rate, and the same effect of the division can be obtained also on sensing signals sent from the electric conductivity measuring cells. If the sensing signals themselves thus created are added or subtracted, the multiplication or the division is included in the addition or the subtraction, and, when the sensing signals themselves are treated, as needed, it also becomes possible that addition, subtraction, multiplication and division are combined arbitrarily. The signal created after treating the sensing signals themselves sent from the electric conductivity measuring cells as described above can be amplified in order to optimize the level of the output signal, as needed, and in such a case, because an object is the single signal after the treatment, a single amplifier may be provided.

Further, in the multiple electric conductivity measuring apparatus according to the present invention, it may be constituted that each of the electric conductivity measuring cells has three electrodes, the three electrodes include an electric conductivity detection electrode and two AC current supply electrodes disposed on both sides of the electric conductivity detection electrode at respective distances, and an AC current of the same phase is applied to the two AC current supply electrodes. Alternatively, it may be constituted that each of the electric conductivity measuring cells has three electrodes, the three electrodes include an electric conductivity detection electrode, an AC current supply electrode disposed on one side of the electric conductivity detection electrode at a distance, and a grounded electrode disposed on the other side of the electric conductivity detection electrode at a distance. By such three-electrode constitutions, a high-accuracy measurement, free from adverse effects from circumstances such as noises, becomes possible, as described later.

Further, in the multiple electric conductivity measuring apparatus according to the present invention, it is preferred that the above-described at least two electrodes in each electric conductivity measuring cell are constructed so that their electrode surfaces are formed by titanium oxide layers on surfaces of electrode bodies made of a conductive metal. In such a constitution, when organic substances and the like are contained in a substance to be measured, the property for decomposing organic substances based on the photocatalytic activity of the titanium oxide, and its super-hydrophilicity can be effectively utilized, in order to eliminate adverse effects on the measurement of the electric conductivity due to the adhesion or adsorption of the organic substances to the electrode surfaces. It is preferred that light irradiating means is disposed against the titanium oxide layers to provide a photocatalytic activity to the titanium oxide layers. For example, each electric conductivity measuring cell can be constructed so as to have a space for storing a substance to be measured defined between respective electrode surfaces of the above-described at least two electrodes, and light irradiating means that irradiates light onto the respective electrode surfaces.

In this multiple electric conductivity measuring apparatus, it is preferred that light irradiated by the above-described light irradiating means has a wavelength which brings about a photocatalytic activity of the above-described titanium oxide layers. For example, light with a wavelength from about 300 to about 400 nm can be employed. As the light irradiating means, a light source composed of means for irradiating ultraviolet rays and the like such as a black light may be directly employed, and a light guiding material (for example, an optical fiber, or tube and the like comprising a light guiding raw material) to guide light from a light source provided as means for irradiating light may also be employed. Further, the light from a light guiding material may be added to light irradiated directly from a light source.

Further, the above-described space for storing a substance to be measured may be defined by a light transmitting material, and it may be constituted so that the light from the light irradiating means is irradiated onto an electrode surface through the light transmitting material (for example, glass). In this case, if a titanium oxide coating layer capable of transmitting light is provided on the surface of the light transmitting material at its side facing the space for storing a substance to be measured (a surface in contact with solution), adhesion of organic substances and the like to this surface of the light transmitting material can be prevented by super-hydrophilicity and organics decomposition property ascribed to the titanium oxide layer.

Further, the above-described electrode can be produced by, for example, the following method. Namely, a method can be employed wherein an electrode surface is formed by providing on a titanium oxide layer on a surface of an electrode body made of a conductive metal by a surface treatment such as sputtering, plating or the like. Alternatively, a method can also be employed wherein an electrode surface made of a titanium oxide layer is formed by providing oxygen to a surface of an electrode body made of titanium. As the method for forming a titanium oxide layer by providing oxygen, a method based on air oxidation other than a method utilizing electrolysis can be employed.

In the multiple electric conductivity measuring apparatus according to the present invention as described above, a treatment of at least either addition or subtraction is added to the sensing signals themselves sent from the respective electric conductivity measuring cells in the apparatus, and the signal created after the treatment is output as a single sensing signal. A treatment such as amplification and the like is added to this sensing signal, as needed. The sensing signal thus output corresponds to a difference between the detected electric conductivities at positions set with the respective electric conductivity measuring cells, or a variation between the detected electric conductivities at positions set with the respective electric conductivity measuring cells. It is possible that both of the detected electric conductivities are measured at a substantially same condition or same measuring range, it is not necessary to adjust this condition or measuring range to be met with the scale of the absolute value of the electric conductivity, and it may be adjusted depending on the scale of the above-described difference or variation. Therefore, even when the above-described difference or variation is fine relatively to the scale of the absolute value of the electric conductivity, the micro difference or variation can be extracted with a high accuracy and a high sensitivity. Besides, as described above, since the sensing signals themselves from the respective electric conductivity measuring cells when electrically calculating the difference or variation are signals extracted at a substantially same adjustment condition within a single apparatus, a difference in effect due to the adjustment of the measuring range and the like is not generated between the sensing signals themselves from the respective electric conductivity measuring cells which are the sources of the calculation. Therefore, also from this point of view, it is guaranteed that the above-described difference or variation is extracted accurately, and it can ensure very highly reliable data.

Thus, in the multiple electric conductivity measuring apparatus according to the present invention, since sensing signals themselves from the respective electric conductivity measuring cells can be treated to be at least added and/or subtracted, the measuring apparatus can measure a micro difference or variation of the electric conductivity between a plurality of measuring points different in position or time with a high accuracy and a high sensitivity, and an extremely high-reliability data can be obtained with respect to the measurement of electric conductivity.

THE BEST MODE FOR CARRYING OUT THE INVENTION

Hereinafter, preferred embodiments of the present invention will be explained referring to Figures.

Figure 1:
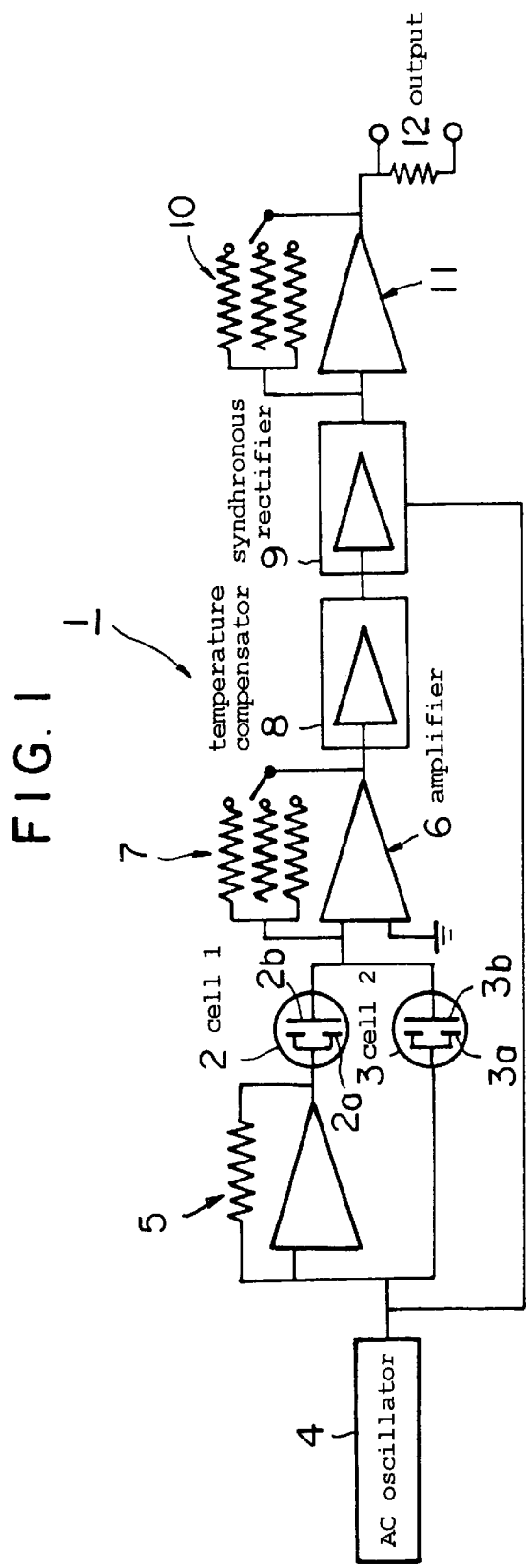
FIG. 1 is an electric circuit diagram of a multiple electric conductivity measuring apparatus according to an embodiment of the present invention.

FIG. 1 shows an electric circuit constitution of a multiple electric conductivity measuring apparatus according to an embodiment of the present invention. In FIG. 1, a multiple electric conductivity measuring apparatus 1 has at least two electric conductivity measuring cells (in this embodiment, a two-cell constitution is depicted) each having at least two electrodes (in this embodiment, a three-electrode constitution is depicted) brought into contact with a substance to be measured. In this embodiment, the electric conductivity measuring cells 2, 3 (FIG. 1 indicates them as "cell 1" and "cell 2", respectively) are connected electrically so that sensing signals themselves from the electric conductivity measuring cells 2, 3 can be treated to be added.

The electric conductivity measuring cells 2, 3 are connected electrically in parallel with each other, and an AC current with the same phase is supplied from an AC oscillator 4 provided as a power source to electric current supply electrodes 2a, 3a of the respective electric conductivity measuring cells 2, 3. The electric conductivity detection electrodes 2b, 3b of the respective electric conductivity measuring cells 2, 3 are electrically connected to each other, and the detection signals themselves from the electric conductivity detection electrodes 2b, 3b can be added. In this embodiment, a multiplication unit or division unit 5 for multiplying the value of AC current to be supplied at a predetermined magnification or for dividing it with a predetermined rate is provided before the electric conductivity detection electrode 2a of the electric conductivity measuring cell 2, and the level of an electric conductivity of a substance to be measured as an object detected by the electric conductivity measuring cell 2 is made different from that by the electric conductivity measuring cell 3. Namely, an AC current before being supplied to the electric current supply electrode 2a is amplified or attenuated at a predetermined magnification. By this, as described later, in a treatment system, the respective electric conductivities can be detected at optimized sensitivities with respect to the respective detecting positions before the treatment and after the treatment (for example, after concentration or after dilution).

The signal obtained after the above-described treatment of the electric calculation, namely, the signal obtained from a coupled point of the electric conductivity detection electrodes 2a, 3a, is amplified to an appropriate level suitable as an output signal, by a single amplifier 6. At this juncture, an optimum measuring range can be selected depending upon the measurement object by a measuring range switching unit 7.

In this embodiment, the signal sent from amplifier 6 is synchronized with the output side of the AC current oscillator 4 by a synchronous rectifier 9, after a temperature compensation for the measurement environment is performed by a temperature compensator 8. Further, the signal is amplified by an amplifier 11 with a range controller 10 so as to become a signal with an optimum level for a certain kind of control or display of output, and it is extracted as an actual output 12.

Figure 2:
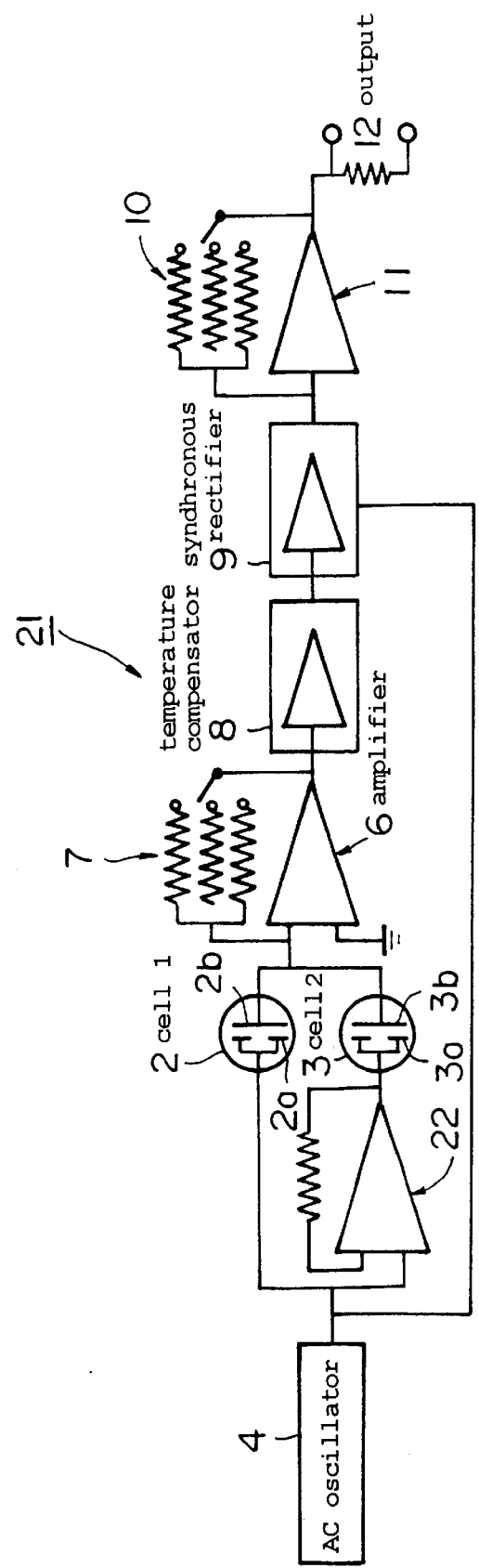
FIG. 2 is an electric circuit diagram of a multiple electric conductivity measuring apparatus according to another embodiment of the present invention.

FIG. 2 shows an electric circuit of a multiple electric conductivity measuring apparatus according to another embodiment of the present invention. In a multiple electric conductivity measuring apparatus 21 according to this embodiment, as compared with the embodiment shown in FIG. 1, a multiplication unit or division unit 22 for multiplying AC current to be supplied at a predetermined magnification or for dividing it with a predetermined rate is provided before the electric conductivity detection electrode 3a of the electric conductivity measuring cell 3, and the level of an electric conductivity of a substance to be measured as an object detected by the electric conductivity measuring cell 3 is made different from that by the electric conductivity measuring cell 2. A phase reversing function is provided to this multiplication unit or division unit 22. Namely, AC current before being supplied to the electric current supply electrode 3a is amplified or attenuated at a predetermined magnification, and at the same time, the phase of the supplied AC current is reversed. By this, the sensing signals themselves from the respective electric conductivity measuring cells 2, 3 are substantially subtracted, and the signal treated by the subtraction is sent to the amplifier 6. Other constitutions are the same as those shown in FIG. 1.

Figure 3:
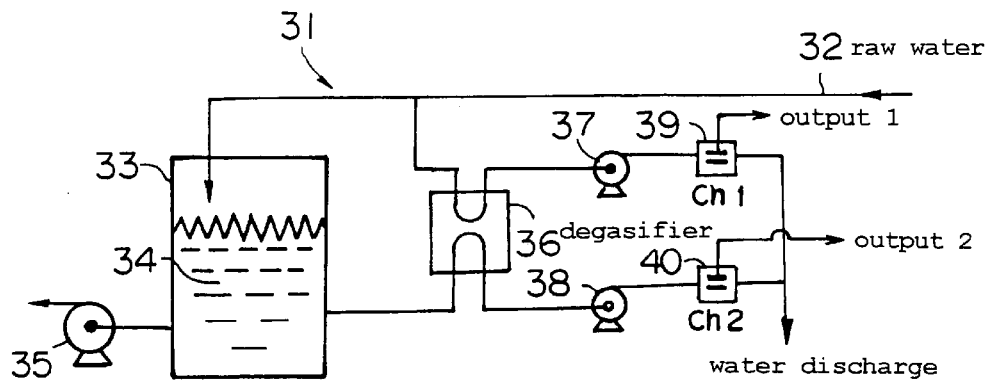
FIG. 3 is a schematic view of a water treatment system which incorporates a multiple electric conductivity measuring apparatus according to the present invention.

The multiple electric conductivity measuring apparatus constructed as described above is used, for example, as shown in FIG. 3. FIG. 3 shows a water treatment system 31, the system has a tank 33 for storing concentrated or diluted water (for example, a cooling tower, a dilution reservoir and the like) against raw water 32. The stored water 34 is sent by a pump 35 from the tank 33 to a next treatment system or operation system. In such a water treatment system 31, when measured is a difference of electric conductivity or a variation of electric conductivity between the raw water 32 and the concentrated or diluted water in the tank 33 (hereinafter, referred to as concentrated water and the like 34) is to be measured as shown in FIG. 3, the raw water 32 and the concentrated water and the like 34 are taken out as sample waters through a degasifier 36. Sampled raw water 32 and concentrated water and the like 34 are sent to electric conductivity measuring cells 39, 40 (which correspond to the aforementioned electric conductivity measuring cells 2, 3 channel 1 (ch1), channel 2 (ch2)), respectively, and the electric conductivities are measured. The waters after measurement are discharged, or returned to an appropriate recycle system.

In this case, although the sensing signals sent from the respective electric conductivity measuring cells 39, 40 can be extracted as absolute values of the electric conductivities of the raw water 32 and the concentrated water and the like 34, respectively, in the present invention, mainly sensing signals (output 1, output 2 in the Figure) detected by the electric conductivity measuring cells 39, 40 receive the treatment of the electric calculation as aforementioned, and the treated signal is detected as a difference or variation of electric conductivities at the both detecting positions.

Figure 4:
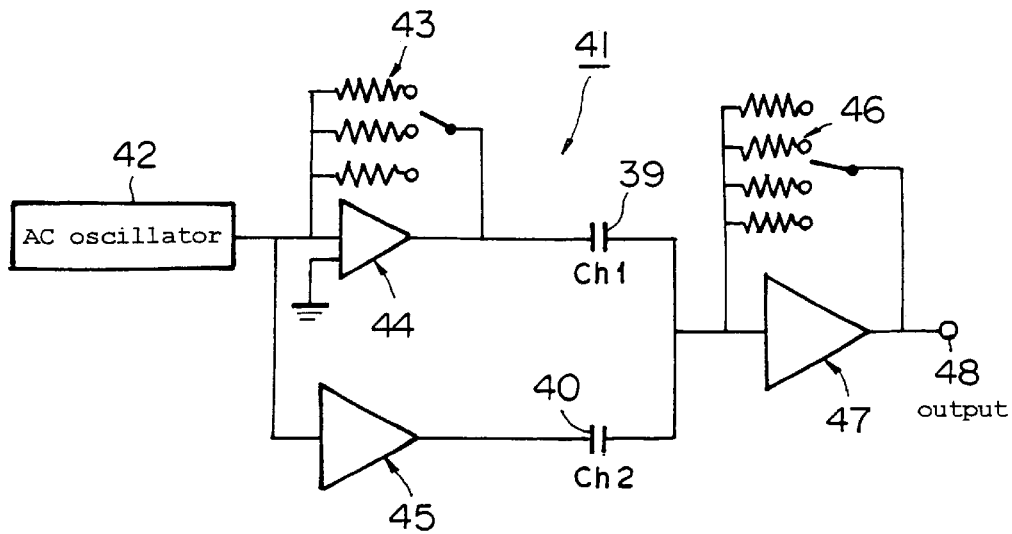
FIG. 4 is an electric circuit diagram showing an example of a multiple electric conductivity measuring apparatus according to the present invention usable for conductivity measurement in the water treatment system depicted in FIG. 3.

In the detection system shown in FIG. 3, a multiple electric conductivity measuring apparatus 41 as shown in FIG. 4, for example, is constituted. In the multiple electric conductivity measuring apparatus shown in FIG. 4, an AC current from an AC oscillator 42 is supplied to the respective electric conductivity measuring cells 39, 40. An AC current, which is amplified by a phase reversing amplifier 44 with a magnification setting unit 43 at a predetermined magnification and the phase of which is reversed, is supplied to one electric conductivity measuring cell 39. To the other electric conductivity measuring cell 40, an AC current amplified at a constant magnification by an amplifier 45 is supplied without reversing its phase. The output sides of the respective electric conductivity measuring cells 39, 40 are connected to each other, and since the phase of the above-described one supplied AC current is reversed, a subtraction treatment is conducted to create a difference between the sensing signals sent from both of the electric conductivity measuring cells 39, 40. This subtraction treated signal is amplified by an amplifier 47 with a sensitivity (measuring range) switching unit 46, and output as a single output signal 48. Therefore, this output signal 48 indicates a difference or variation between the detected electric conductivities of both of the electric conductivity measuring cells 39, 40.

Thus, since the difference or the variation is not calculated from the absolute values of the sensing signals output from the respective electric conductivity measuring apparatuses, but the subtraction treatment is performed with respect to the sensing signals themselves from the respective electric conductivity measuring cells 39, 40 in a single multiple electric conductivity measuring apparatus 41, only the difference or variation between electric conductivities of both of the electric conductivity measuring cells 39, 40 can be extracted accurately. Further, because the measuring range at the time of this measurement may be adjusted not relative to the absolute value of electric conductivity but relative to the difference or variation of electric conductivity to be detected, even if the difference or variation is much smaller than the absolute value of electric conductivity, the adjustment to an optimum measuring range regardless to the absolute value of electric conductivity is possible, and an extremely high-accuracy and high-sensitivity measurement becomes possible.

Further, since the level of the current supplied to one electric conductivity measuring cell 39 can be appropriately switched by the magnification switching unit 43, an optimum adjustment of sensitivity can be performed for any of a concentration system or a dilution system. Moreover, since the sensitivity (measuring range) switching unit 46 is provided also on the output side, the level of the signal finally output can also be adjusted to an optimum level, and the data of the difference or variation of electric conductivity can be determined at an optimum sensitivity. As a result, extremely high-reliability data of the difference or variation in the electric conductivity measurement can be obtained with a high accuracy and a high sensitivity.

In the measurement system shown in FIG. 3, although the difference or variation of the electric conductivity measurement between different two positions sandwiching a water treatment system is measured, in the present invention a variation with time of the electric conductivity measurement in a flow direction of a substance, for example, can be measured.

Figure 5:
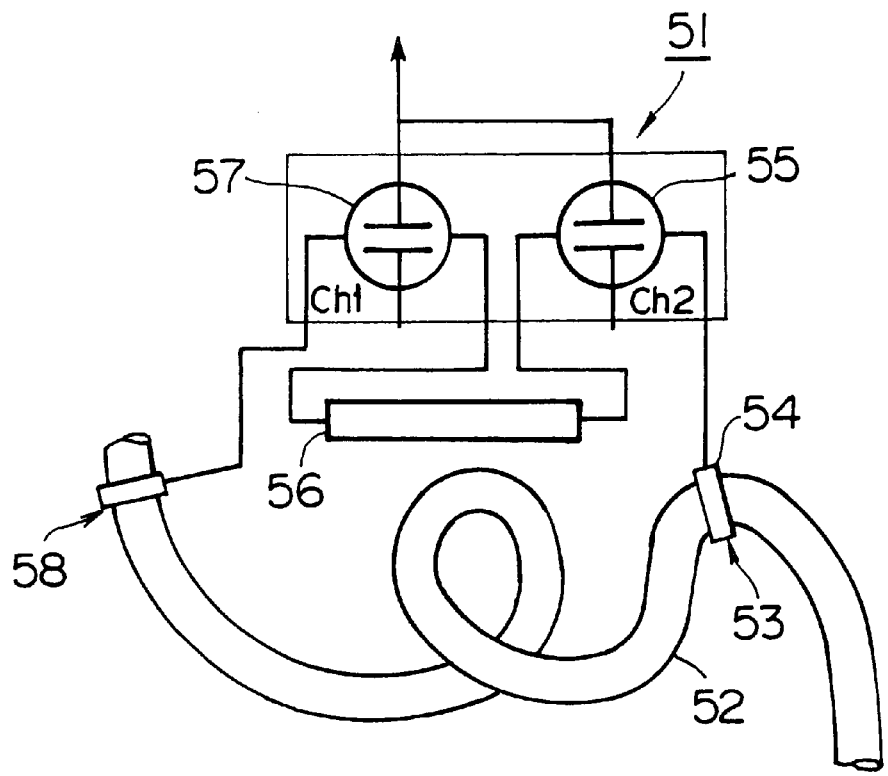
FIG. 5 is a schematic view showing an example of a multiple electric conductivity measuring apparatus according to the present invention in which a time delay column is used.

For example, as shown in FIG. 5, when a variation of electric conductivity measurement between different positions is measured in the flow direction of the water flowing in a water flow tube 52, a multiple electric conductivity measuring apparatus 51 is disposed to take out a sample water through, for example, a Venturi tube 54 at an upstream position 53. After the electric conductivity of this sample water is at first detected by one electric conductivity measuring cell 55, the sample water is sent to the other electric conductivity measuring cell 57 through a time delay column 56, the electric conductivity of the sample water is measured again in this cell 57, and the sample water after the measurement is returned to a downstream position 58 of the water flow tube 52. The time delay column 56 is designed to adjust a residual time from an end of inlet to an end of outlet by, for example, winding a capillary spirally, and in this embodiment, the residual time is adjusted to substantially correspond to a flow time from the upstream position 53 to the downstream position 58 of the water flow tube 52.

By providing such time delay column 56 and timely shifting the timing of electric conductivity detection as to an identical sample water, it can be observed how the electric conductivity varies between these two different times. And, by employing the multiple electric conductivity measuring apparatus 51 according to the present invention for this observation, the variation of electric conductivity is detected with a high reliability, a high accuracy and a high sensitivity.

In the present invention, the structures of the respective electric conductivity measuring cells are not particularly restricted, and they may be each constructed to have at least two electrodes brought into contact with a substance to be measured. In the case where two electrodes are used in each electric conductivity measuring cell, one is an electric conductivity detection electrode and the other is an electric current supply electrode, and when three-electrode constitution is employed, one of the three electrodes can be formed as a grounded electrode. Although it is preferred that an AC current is supplied to the electric current supply electrode, a constitution for supplying a DC current can also be employed.

Figure 6:
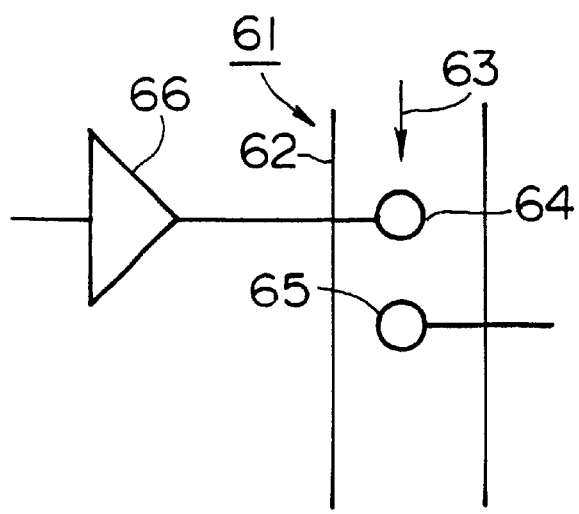
FIG. 6 is a schematic diagram showing an example of an electric conductivity measuring cell usable for a multiple electric conductivity measuring apparatus according to the present invention.

FIG. 6 shows a schematic constitution of an electric conductivity measuring cell having a two-electrode formation applicable to the present invention. In the electric conductivity measuring cell 61 shown in FIG. 6, a power supply electrode 64 and an electric conductivity detection electrode 65 are disposed at a distance in a fluid 63 to be measured and flowing in a measurement tube 62 or being stored in the tube 62. An AC current is applied to the power supply electrode 64 from, for example, a power source (not shown) through an amplifier 66, and a detection current from the electric conductivity detection electrode 65 receives the treatment of the aforementioned addition or subtraction.

In the electric conductivity measuring cell 61 of two-electrode formation as described above, the measuring tube 62 is composed of an insulation material (for example, a vinyl chloride tube) at least at the position of the above-described electric conductivity measurement, since the system is often substantially in a grounded condition at any position of the extending portion of the tube, noises may be picked up from the environment, originating from the grounded condition.

Figure 7:
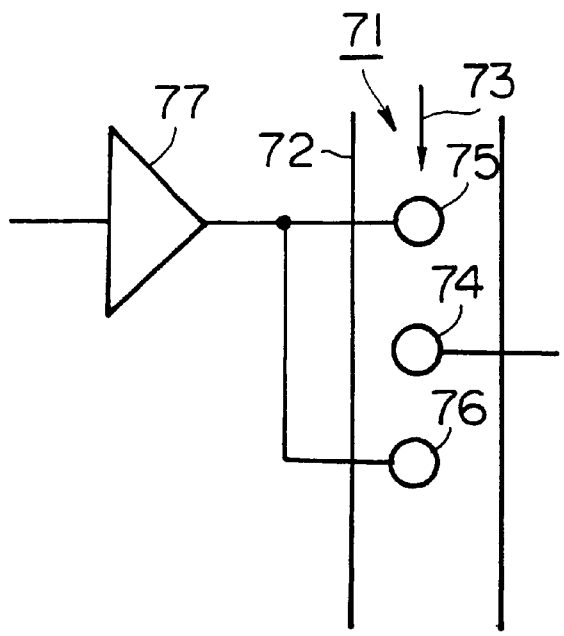
FIG. 7 is a schematic diagram showing another example of an electric conductivity measuring cell usable for a multiple electric conductivity measuring apparatus according to the present invention.
Figure 8:
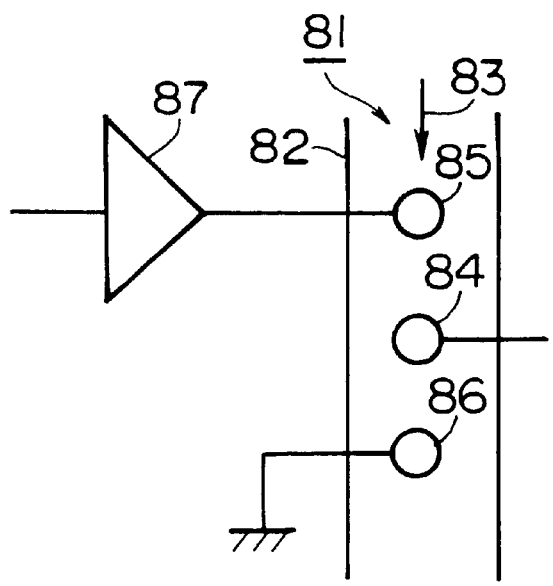
FIG. 8 is a schematic diagram showing a further example of an electric conductivity measuring cell usable for a multiple electric conductivity measuring apparatus according to the present invention.

In order to remove any effect ascribed to such noises, it is preferred that electric conductivity measuring cells having three-electrode constitutions, for example, as shown in FIGS. 7 and 8, are used. In an electric conductivity measuring cell 71 shown in FIG. 7, three electrodes 74, 75, 76 brought into contact with a fluid 73 to be measured are provided in the fluid 73 to be measured and flowing in an insulated measuring tube 72 or being stored in the measuring tube 72. The three electrodes comprise an electric conductivity detection electrode 74 for detecting electric conductivity and two AC current supply electrodes 75, 76 disposed on both sides of the electric conductivity detection electrode 74 at respective distances. AC current of the same phase is applied with a constant voltage and the same potential to the two AC current supply electrodes 75, 76 through an amplifier 77. The detected current from the electric conductivity detection electrode 74 receives the treatment of the aforementioned addition or subtraction.

In the electric conductivity measuring cell 71 shown in FIG. 7, the electric conductivity measuring electrode 74 is electrically shielded against a grounded point which would exist at any point of the extending portion of the measurement tube 72 by the two AC current supply electrodes 75, 76, which are disposed on both sides of the electric conductivity detection electrode 74, and to which an AC current of the same phase is supplied. Namely, since a constant voltage AC current with the same phase is applied to the two AC current supply electrodes 75, 76, and the potential difference between the electric conductivity detection electrode 74 and the AC current supply electrode 75, 76 is always maintained at a predetermined constant value, substantially no electric resistance exists between the electric conductivity detection electrode 74 and an outside grounded point. Therefore, any resistance between an electric conductivity detection electrode and an outside grounded point, and any influence on an output electric current from the electric conductivity detection electrode originating from a variation of any such resistance, as in the cell constitution shown in FIG. 6, disappear substantially completely. In other words, any leaked electric current from the electric conductivity detection electrode 74 to the outside grounded point does not exist at all. As a result, the output electric current from the electric conductivity detection electrode 74 is extracted at a condition with no disturbance at all times, and dispersion and variation due to the disturbance are prevented, thereby ensuring a stable and high-accuracy measurement of electric conductivity at all times.

In the electric conductivity measuring cell 81 shown in FIG. 8, three electrodes 84, 85, 86 brought into contact with a fluid 83 to be measured are provided in the fluid 83 flowing in an insulated measurement tube 82 or being stored in the measurement tube 82. The three electrodes comprise an electric conductivity detection electrode 84 for detecting electric conductivity and an AC current supply electrode 85 disposed on one side of the electric conductivity detection electrode 84 at a distance, and a grounded electrode 86 disposed on the other side of said electric conductivity detection electrode 84 at a distance. An AC current with the phase is applied at a constant voltage to the AC current supply electrodes 85 through an amplifier 87. The detected current from the electric conductivity detection electrode 84 receives the treatment of the aforementioned addition or subtraction.

In the electric conductivity measuring cell 81 shown in FIG. 8, an AC current with a constant voltage is supplied only to the AC current supply electrode 85, the grounded electrode 86 is forcibly made to be zero in potential by the grounding, and these electrodes 85, 86 are disposed on both sides of the electric conductivity detection electrode 84. Therefore, the portion between the electrodes 85, 86 is divided in electrical circuit in a formation of a so-called resistive division, by the electric conductivity detection electrode 84. In the circuit between these electrodes 85, 86, a predetermined AC current with a constant voltage is applied to the electrode 85, and the potential of the electrode 85 is always forced to be zero, and this condition is always maintained stably. Namely, even if any extending portion of the measurement tube 82 is grounded, there is no room to allow a resistance to enter between the grounded point and the electric conductivity detection electrode 84, thereby preventing the electric current extracted from the electric conductivity detection electrode 84 from shifting or varying. Therefore, the output electric current from the electric conductivity detection electrode 84 is extracted at a condition with no disturbance at all times, and dispersion and variation due to the disturbance are prevented, thereby ensuring a stable and high-accuracy measurement of electric conductivity at all times.

Figure 9:
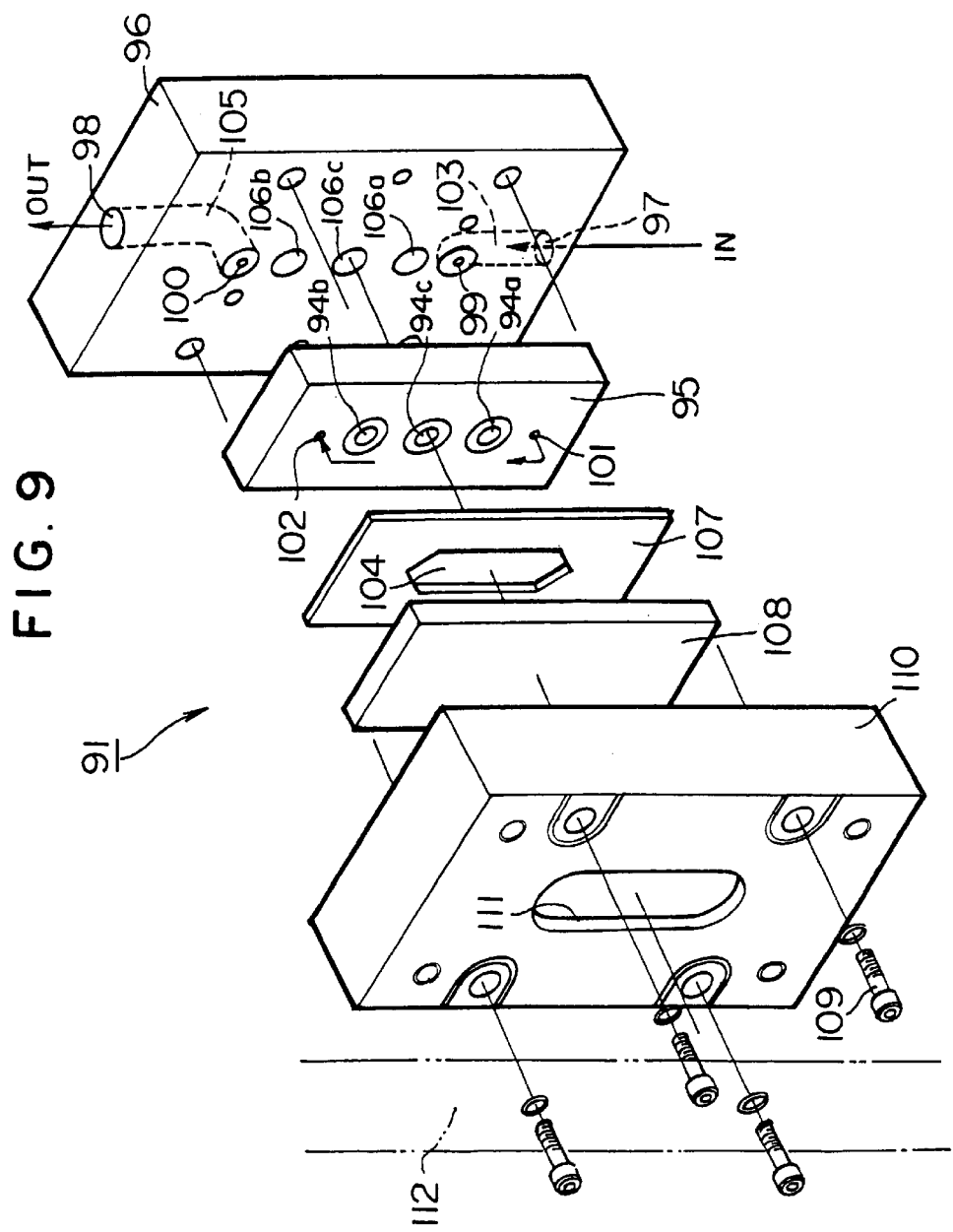
FIG. 9 is an exploded perspective view showing an example of the mechanical constitution of an electric conductivity measuring cell usable for a multiple electric conductivity measuring apparatus according to the present invention.
Figure 10:
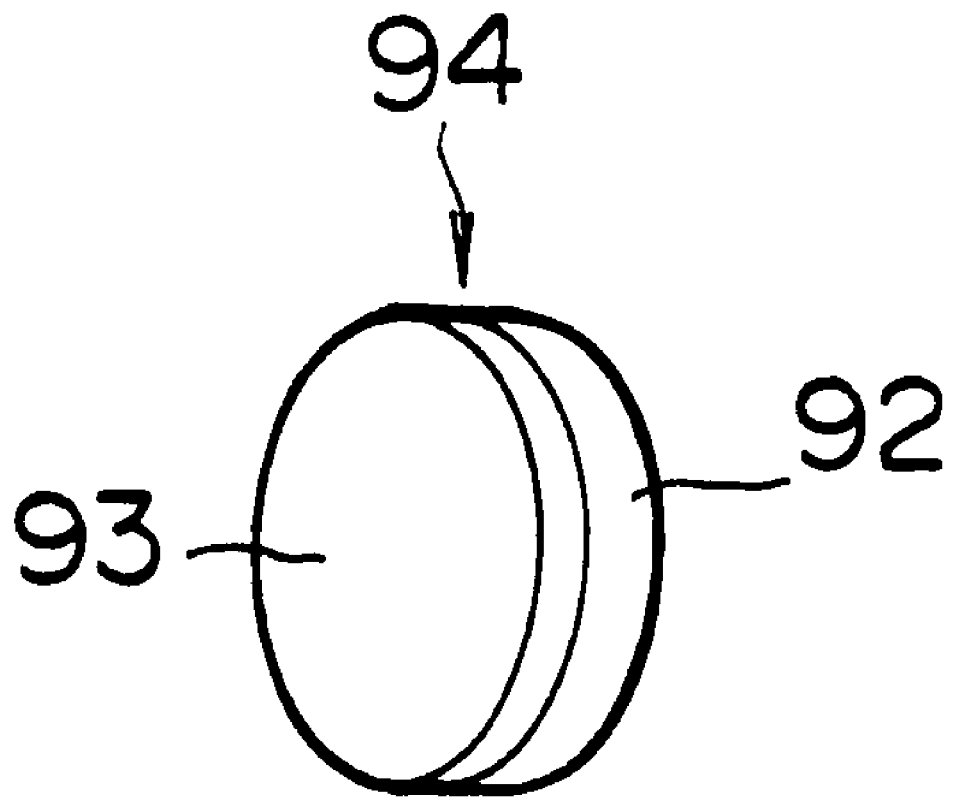
FIG. 10 is a perspective view showing an example of the constitution of an electrode of an electric conductivity measuring cell usable for a multiple electric conductivity measuring apparatus according to the present invention.

In the present invention, the mechanical construction of an electric conductivity measuring cell is not particularly restricted, and it can be formed as a construction shown in FIG. 9 for example. In the electric conductivity measuring cell 91 shown in FIG. 9, an electric conductivity measuring electrode 94 shown in FIG. 10 is preferably used for example, wherein an electrode surface is formed by a titanium oxide layer 93 on the surface of an electrode body 92 made of a conductive metal. The titanium oxide layer 93 is formed by a surface treatment such as sputtering, plating and the like, or is formed by oxidizing the surface of the electrode body 92 made of a titanium metal. The oxidation is conducted by electrolysis or air oxidation.

The electric conductivity measuring electrodes 94 are used as electrodes corresponding to two or three electrodes shown in FIGS. 6 to 8, and are attached to an electrode holder 95 made of an insulation material in a condition where the electrode surfaces are exposed as shown in FIG. 9. Three electrodes 94 are disposed in a raw, and the electrodes 94a and 94b at both sides constitute AC current supply electrodes connected to a power source, and the electrode 94c at the central position constitutes an detection electrode functioning as a sensor for detecting electric conductivity.

Electrode holder 95 is fixed at a predetermined position of a substrate 96. In the substrate 96, inlet 97 for introducing a fluid to be measured (for example, an aqueous solution), outlet 98 for discharging the fluid, and flow holes 99 and 100 for measuring electric conductivity are provided. In the electrode holder 95, flow holes 101 and 102 are provided, and the flow hole 101 is disposed to communicate with the flow hole 99 of the substrate, and the flow hole 102 is disposed to communicate with flow hole 100 of the substrate, respectively. A fluid to be measured introduced from inlet 97 is sent into a space 104 for storing a substance to be measured, which is defined on the side of the electrode surfaces of the respective electrodes 94 through an inside path 103 of the substrate 96, the flow hole 99, and the flow hole 101 of electrode holder 95. The space 104 for storing a substance to be measured forms a flow path for measuring electric conductivity of a fluid to be measured. The fluid from the space 104 for storing a substance to be measured is discharged from outlet 98 through the flow hole 102 of electrode holder 95, the flow hole 100 of the substrate 96, and an inside path 105.

In the substrate 96, through holes 106a, 106b, 106c are opened at positions corresponding to the respective electrodes 94a, 94b, 94c, and necessary electric wires are pulled out of the through holes 106a, 106b, 106c.

The space 104 for storing a substance to be measured, in this embodiment, is defined by a sheet-like packing 107, and a transparent glass plate 108 provided as a light transmitting material which is disposed to confront electrode holder 95 with a gap via packing 107. It is preferred that a titanium oxide coating layer is provided to such an extent that the light transmitting property is not damaged, also to the surface of glass plate 108 on its side facing the space 104 for storing a substance to be measured. The electric conductivity of the fluid, flowing in this space 104 for storing a substance to be measured, is measured.

Electrode holder 95, packing 107 and glass plate 108 are fixed to a cover body 110 on one surface side of substrate 96 by bolts 109. A window 111 for transmitting light is opened on cover body 110. Through this window 111, light from light irradiating means 112 which is disposed outside is irradiated. Light irradiated is shed on titanium oxide layers 93 that form the electrode surfaces of the respective electrodes 94a, 94b, 94c through glass plate 108 from the window 111. Light having a wavelength that brings about a photocatalytic activity of titanium oxide layers 93 is selected as the light to be irradiated. For example, an ultraviolet ray with a specified wavelength (for example, a wavelength falling within a range of 300 to 400 nm) can be employed, and as light irradiating means 112, a black light that irradiates ultraviolet rays for example, can be used.

If such an electric conductivity measuring cell 91 is constituted, by irradiating light from light irradiating means 112, titanium oxide layers 93 provided on the surfaces of the respective electrodes 94a, 94b, 94c exhibit a photocatalytic activity, and even when organic substances are contained in a fluid to be measured flowing in the space 104 for storing a substance to be measured, the organic substances are decomposed by the photocatalytic activity. Therefore, even if ion exchange is performed on the electrode surfaces during the measurement of electric conductivity, the non-conductive organic substances are prevented from adhering or being adsorbed onto the electrode surfaces. As a result, a periodical cleaning of the electric surfaces is not required any more, and electric conductivity can be measured stably and accurately at all times without any cleaning. Further, repeatability of such a high-accuracy measurement can also be ensured.

Further, if a titanium oxide coating layer is provided on the surface of glass plate 108 on its side facing the space 104 for storing a substance to be measured, the adhesion or adsorption of organic substances to this surface side is also prevented, and accumulation of the organic substances in the space 104 for storing a substance to be measured is prevented, thereby maintaining the high-accuracy measurement.

Figure 11:
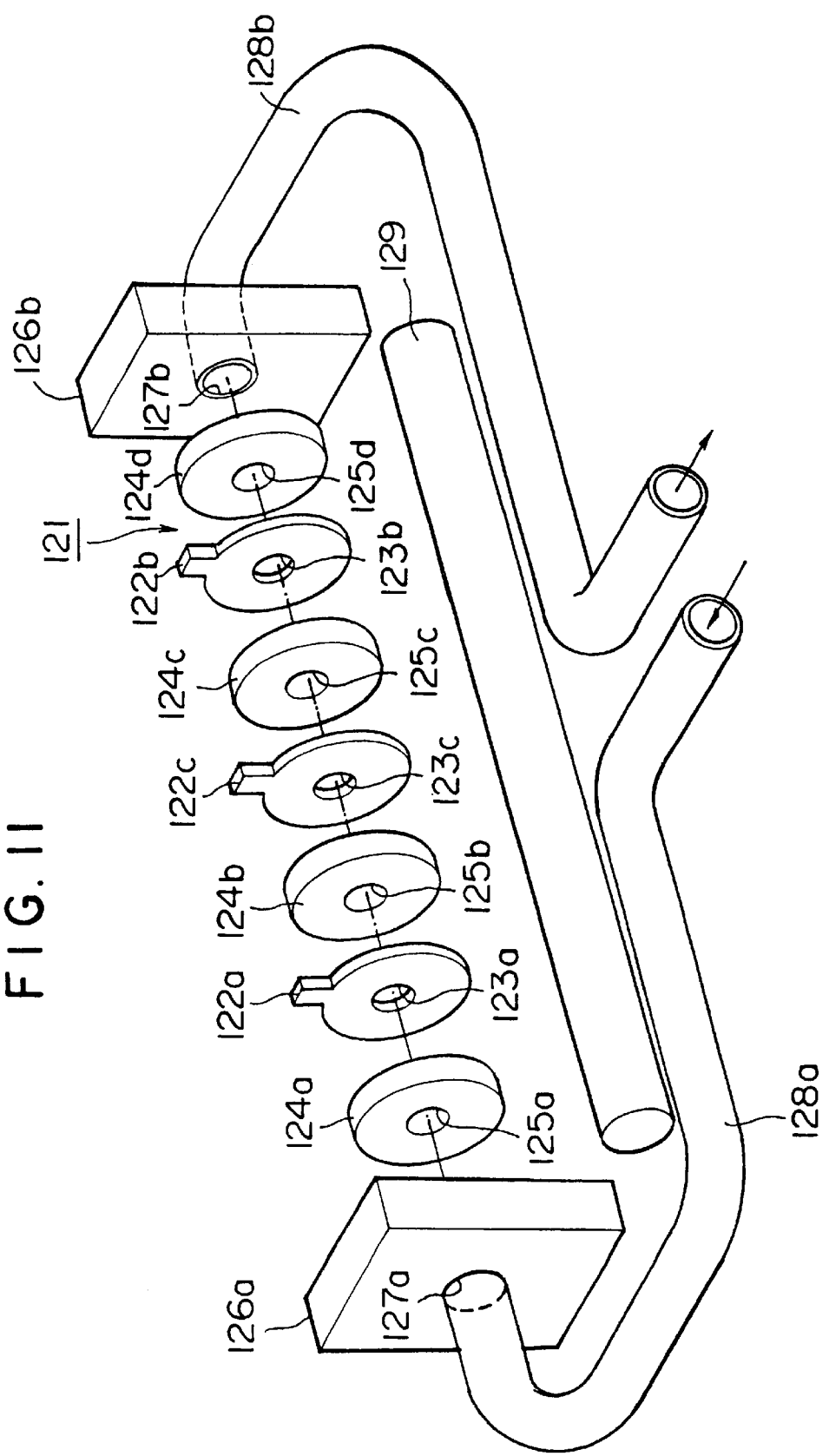
FIG. 11 is an exploded perspective view showing another example of the mechanical constitution of an electric conductivity measuring cell usable for a multiple electric conductivity measuring apparatus according to the present invention.

The structure of the portion of the electric conductivity measuring cell is not limited to that shown in FIG. 9, and, for example, it can also be constructed as shown in FIG. 11. In the electric conductivity measuring cell 121 shown in FIG. 11, three electrodes 122a, 122b, 122c are provided, and for example, the electrode 122a, 122b on both sides are constituted as power supplying electrodes connected to a power source, and the electrode 122c disposed between them is constituted as a detection electrode functioning as a sensor for detecting an electric conductivity. Through holes 123a, 123b, 123c are opened at the central portions of the respective electrodes 122a, 122b, 122c, and titanium oxide layers are provided on the inner surfaces of the respective holes 123a, 123b, 123c. Spacers 124a, 124b, 124c, 124d made of a light transmitting insulation material (for example, 4-fluoride ethylene) are disposed on both sides of the respective electrodes 122a, 122b, 122c, and the respective electrodes and spacers are stacked alternately. Through holes 125a, 125b, 125c, 125d are opened also in the central portions of spacers 124a, 124b, 124c, 124d, respectively. Support materials 126a, 126b are disposed outside of spacers 124a, 124d positioned at both sides, and a stacked body comprising the electrodes 122a, 122b, 122c, and the spacers 124a, 124b, 124c, 124d are sandwiched from both sides by the support materials. Through holes 127a, 127b are opened also in the central portions of the respective support materials 126a, 126b, and into the holes 127a, 127b, one end of a tube 128a for introducing a fluid to be measured, and one end of a tube 128b for discharging the fluid are inserted and fixed, respectively.

A flow path of a fluid to be measured is formed by holes 125a, 123a, 125b, 123c, 125c, 123b, 125d connected by stacking the electrodes 122a, 122b, 122c and the spacers 124a, 124b, 124c, 124d. A fluid to be measured introduced through tube 128a is discharged through tube 128b, after flowing inside of this flow path. These tubes 128a, 128b are composed of a light transmitting material (for example, 4-fluoride ethylene), and an ultraviolet ray with a predetermined wavelength is irradiated from black light 129 provided as means for irradiating light. As the ultraviolet ray irradiated repeats diffusion and reflection in tubes 128*a*, 128*b* as well as transmits the tubes, the ultraviolet ray is guided along the tubes 128*a*, 128*b*, and guided to the inner surfaces formed by titanium oxide layers in the respective electrodes 122*a*, 122*b*, 122*c* from the portions of holes 127*a*, 127*b* at both sides. Further, as the respective spacers 124*a*, 124*b*, 124*c*, 124*d* are also composed of a light transmitting material, the ultraviolet ray from black light 129 is irradiated to the inner surfaces of electrodes 122*a*, 122*b*, 122*c* after transmitting each spacer while utilizing diffusion and reflection. Especially, by forming each electrode and spacer to be relatively thin (for example, the thickness of each electrode is about 0.2 mm, and the thickness of each spacer is about 1 mm), because the flow path formed by the respective electrodes and spacers becomes relatively short, even if a particular light transmitting material such as an optical fiber is not used, a sufficient amount of light for measurement is irradiated onto predetermined electrode surfaces by the light guiding along light transmitting tubes 58*a*, 58*b* as described above, and by the light guiding through light transmitting spacers 124*a*, 124*b*, 124*c*, 124*d*. Therefore, in this embodiment, a simpler and smaller unit can be constructed.

INDUSTRIAL APPLICATION OF THE INVENTION

In the multiple electric conductivity measuring apparatus according to the present invention, a micro difference or variation of electric conductivity between a plurality of measuring points different in position or time can be determined with a high reliability, a high accuracy and a high sensitivity. Therefore, the multiple electric conductivity measuring apparatus according to the present invention is extremely useful particularly for measurement of a micro difference or variation of electric conductivity between a plurality of measuring points in a water treatment system, thereby obtaining reliable measured data at a high accuracy and a high sensitivity.

What is claimed is:

1. A multiple electric conductivity apparatus comprising at least two electric conductivity measuring cells each having at least two electrodes brought into contact with a substance to be measured, said electric conductivity measuring cells being so connected electrically that sensing signals themselves from said electric conductivity measuring cells are treated to be added and/or subtracted, said at least two electrodes of each of said at least two electric conductivity measuring cells being constructed so that their electrode surfaces are formed by titanium oxide layers on surfaces of electrode bodies made of a conductive material, wherein each electric conductivity measuring cell has a space for storing a substance to be measured which is defined between respective electrode surfaces of said at least two electrodes, and light irradiating means for irradiating light onto the respective electrode surfaces, and wherein said light irradiating means comprises a light guiding material which guides light from a light source.

2. A multiple electric conductivity apparatus comprising at least two electric conductivity measuring cells each having at least two electrodes brought into contact with a substance to be measured, said electric conductivity measuring cells being so connected electrically that sensing signals themselves from said electric conductivity measuring cells are treated to be added and/or subtracted, said at least two electrodes of each of said at least two electric conductivity measuring cells being constructed so that their electrode surfaces are formed by titanium oxide layers on surfaces of electrode bodies made of a conductive material, wherein each electric conductivity measuring cell has a space for storing a substance to be measured which is defined between respective electrode surfaces of said at least two electrodes, and light irradiating means for irradiating light onto the respective electrode surfaces, and wherein said space for storing a substance to be measured is defined by a light transmitting material, and light from said light irradiating means is irradiated onto said electrode surfaces through said light transmitting material.

3. The multiple electric conductivity measuring apparatus according to claim 2, wherein a titanium oxide coating layer capable of transmitting light is provided on a surface of said light transmitting material of its side facing said space for storing a substance to be measured.

* * * * *